United States Patent
Hu et al.

(10) Patent No.: US 10,535,424 B2
(45) Date of Patent: Jan. 14, 2020

(54) METHOD FOR PROACTIVE COMPREHENSIVE GERIATRIC RISK SCREENING

(71) Applicant: International Business Machines Corporation, Armonk, NY (US)

(72) Inventors: Jianying Hu, Bronx, NY (US); Zhaonan Sun, Elmsford, NY (US); Fei Wang, Fremont, CA (US)

(73) Assignee: International Business Machines Corporation, Armonk, NY (US)

( * ) Notice: Subject to any disclaimer, the term of this patent is extended or adjusted under 35 U.S.C. 154(b) by 810 days.

(21) Appl. No.: 15/048,413

(22) Filed: Feb. 19, 2016

(65) Prior Publication Data

US 2017/0242972 A1 Aug. 24, 2017

(51) Int. Cl.
| | |
|---|---|
| *G16H 10/60* | (2018.01) |
| *G16H 50/30* | (2018.01) |
| *G16H 50/50* | (2018.01) |
| *G16H 50/70* | (2018.01) |

(52) U.S. Cl.
CPC .............. *G16H 10/60* (2018.01); *G16H 50/30* (2018.01); *G16H 50/50* (2018.01); *G16H 50/70* (2018.01)

(58) Field of Classification Search
CPC .............. G06F 19/3431; G06F 19/322; G06F 19/3443; G06F 19/3437; G16H 10/60; G16H 50/30; G16H 50/50; G16H 50/70
USPC ....................................... 600/300; 1/1; 705/3
See application file for complete search history.

(56) References Cited

U.S. PATENT DOCUMENTS

| | | | |
|---|---|---|---|
| 7,282,031 B2 | 10/2007 | Hendrich | |
| 2005/0102171 A1 | 5/2005 | Ashley et al. | |

FOREIGN PATENT DOCUMENTS

GB 2352815 A 2/2001

OTHER PUBLICATIONS

Sun al. "LINKAGE: An Approach for Comprehensive Risk Prediction for Care Management". ACM. Aug. 10-13, 2015. pp. 1145-1154.*

(Continued)

*Primary Examiner* — Eunhee Kim
(74) *Attorney, Agent, or Firm* — Scully, Scott, Murphy & Presser, P.C.; Kristofer Haggerty, Esq.

(57) ABSTRACT

An apparatus, method and computer program product for proactive comprehensive generic risk screening. The method performs proactive comprehensive generic risk screening by implementing steps of training comprising steps of receiving cross domain risks and features, optimizing linkage regularization using the received features and the received cross domain risks, said linkage regularization comprising multi-task predictive model training, feature selection and ranking, risk association learning and risk association selection, and outputting patient risk scores, identified high risk patients, risk factors for risks and risk groups, and risk groups and risk associations and calculating risk score for an individual patient comprising steps of receiving individual features comprising patient information, performing said linkage regularization using the received individual features and outputting patient risk scores for said individual patient, and high risk for said individual patient. The calculating risk score can be performed for more than one patient.

17 Claims, 10 Drawing Sheets

(56) References Cited

OTHER PUBLICATIONS

Pavlou et al. "How to develop a more accurate risk prediction model when there are few events". the bmj | BMJ 2015;351:h3868 | doi: 10.1136/bmj.h3868. Jun. 2015. 5 Pages.*

Ellis et al., "Comprehensive geriatric assessment for older adults admitted to hospital: meta-analysis of randomised controlled trials", BMJ, Oct. 2011, pp. 1-10.

Elsawy et al., "The Geriatric Assessment", American Family Physician, Jan. 1, 20111, vol. 83, No. 1, pp. 49-56.

Graf et al. ,"Efficiency and applicability of comprehensive geriatric assessment in the Emergency Department: a systematic review", Aging Clin Exp Res., Oct. 5, 2010, vol. 23, No. 4, pp. 244-254.

Rosen et al., Geriatric Assessment Tools, Mount Sinai Journal of Medicine, Jul./Aug. 2011, vol. 78, Issue 4, pp. 489-497.

* cited by examiner

130

$$\min_{\beta,\Omega} l(Y,X,\beta) + \text{tr}\left[\left(\frac{\lambda_1}{2}\beta^\top\beta + \frac{\lambda_2}{2}\Omega_0\right)\Omega^{-1}\right] + \frac{\lambda_3}{2}\log\det(\Omega)$$

$$+ \gamma\sum_{i\neq j}|\Omega_{ij}|\,\|\beta_i - \text{sign}(\Omega_{ij})\beta_j\|_1 + \gamma_2\|\beta\|_1,$$

$$\text{s.t. } \Omega \succeq 0.$$

BY - PRODUCT: IDENTIFIED RISK FACTORS

GROUP 1 (MENTAL)
RESIDENT IN CONVALESCENT HOME
PRESENT SOCIAL ACTV
OWN TRANSPORTATION EQUIPMENT

GROUP 2 (IADL)
SATISFIED WITH HEALTH CARE SERVICE
EVER HAD SURGERY TO INSERT HEART VALVE
RECEIVE CARE IN HOME
CURRENTLY COVERED BY MEDICARE/MEDICAID
PHYSICAL ACTIVITY

GROUP 3 (ADL)
CHANGE IN SP'S HEALTH STATUS RECENTLY
MEALS ON WHEELS DELIVERED TO HOME

GROUP 4 (NAGI)
OFTEN TROUBLE WITH PAIN
EVER HAD HIP REPLACEMENT SURGERY
EVER HAD KEEN REPLACEMENT SURGERY
HOME OWNED BY OTHERS IN HOUSE HOLD
RESIDENT IN NURSING HOME
HAD KNEE SURGERY RECENTLY

GROUP 5 (MEDICAL)
EVER HAD SURGERY TO INSERT PACEMAKER
HAVE BACK PAIN OR PROBLEMS
HAVE A DOCTOR WHO YOU SEE REGULARLY
SEE DOCTOR IN PAST 12 MONTHS
FOOT SURGERY RECENTLY
HERNIA OPERATION RECENTLY
HAVE BRONCHITIS/EMPHYSEMA
HEART ATTACH RECENTLY
NOW HAVE CANCER

GROUP 6 (SOCIAL)
NUMBER OF LIVING SISTERS
INCOME CHANGE
RADIATION THERAPY RECENTLY
NUMBER OF PRIVATE HEALTH INSURANCE PLANS

GROUP 7 (SENSATION)
ANGIOPLASTY RECENTLY
CHILDREN GIVE MONEY FOR EXPENSES
LIVE IN SUPERVISED APARTMENT

FIG. 5

METHOD FOR PROACTIVE COMPREHENSIVE GERIATRIC RISK SCREENING

FIELD

This disclosure relates generally to a method for proactive comprehensive geriatric risk screening, and particularly to building a computational framework for performing the task of comprehensive geriatric screening as a predictive model using a constrained optimization problem. The method leverages association between vulnerability domains and predicts multiple risks simultaneously, and identifies active risk factors and vulnerability domain associations.

BACKGROUND

Approaches proposed in the current literature for performing assessment are mainly domain-specific assessment tools along with general assessment tools.

Domain-Specific Assessment Tools include techniques for assessing functional ability, such as Activity of Daily Living (ADL), Instrumental Activity of Daily Living (IADL) assessment, Vulnerable Elders Survey (VES-13), and Time Get Up and Go (GUG) evaluation. Other domain-specific assessment tools include techniques for assessing mental health, such as Patient Health Questionnaire (PHQ-9), Geriatric Depression Scale, and Mini Mental State Exam. In addition, assessment tools can assess nutrition, such as Mini Nutritional Assessment (MNA), and physical health, such as Cumulative Illness Rating Scale-Geriatrics.

General Assessment Tools include G-8 Geriatric screening tool which assesses food intake difficulties, weight loss, mobility, neuropsychological problems, BMI, daily prescription drug, self-evaluation of health, age. Another general assessment tool is Triage Risk Screening tool (TRST) for patients over 75 years old; TRST evaluates a patient's history of cognitive impairment, difficult walking/transferring/recent falls, recent ED or hospitalization, lives along/no caregiver, ED staff recommendation.

Yet another general assessment tool is Groningen Frailty Index (GFI) which assesses a patient's mobility, vision, hearing, nutrition, comorbidity, cognition, psychosocial conditions, and physical fitness. Another general assessment tool is Barber screening tool which assesses whether a patient could live alone, could call for help, must depend on someone for regular help, is able to have hot meal, is confined to home, has health concern(s), such as vision or hearing issues, and/or recent hospitalization.

However, all presently known assessment tools have at least the following three limitations. First, all are based on patients' current condition, and do not serve as predictive tools. Second, none of these tools consider domain association. Third, none of these tools identify risk factors or provide future assessments.

SUMMARY

A system, method and computer program product to perform proactive comprehensive geriatric risk screening as a predictive model using a constrained optimization problem is presented.

In one aspect, there is provided a method of performing proactive comprehensive geriatric assessment. The method comprises training a model by receiving at a processing device, data representing cross domain risks; receiving at the processing device, data representing features of multiple patients; receiving at the processing device, data representing complete or incomplete observations in risk targets and features of the multiple patients; optimizing, at the processing device, linkage regularization using the received features, the received cross domain risks data and the complete or incomplete observations data, the linkage regularization comprising multi-task predictive model training, feature selection and ranking, risk association learning and risk association selection; and outputting patient risk scores, identified high risk patients, risk factors for risks and risk groups, and risk groups and risk associations; and calculating a risk score for an individual patient using the trained model comprising: receiving at the processing device, individual features data representing patient information; performing the linkage regularization using the received individual features data; and outputting a patient risk score for one or more target risk types for the individual patient for display via a device providing a user interface.

In one aspect, the training further comprises receiving one or more of expert opinion data, and domain knowledge on risk association data. In one aspect, the calculating risk score is performed for more than one patient.

In a further aspect, there is provided an apparatus for performing proactive comprehensive geriatric risk screening. The apparatus comprises: a memory storage device storing a program of instructions; a processor device receiving the program of instructions to configure the processor device to train a model by: receiving data representing cross domain risks; receiving data representing features of multiple patients; receiving data representing complete or incomplete observations in risk targets and features of the multiple patients; optimizing linkage regularization using the received features, the received cross domain risks and the complete or incomplete observations data, the linkage regularization comprising multi-task predictive model training, feature selection and ranking, risk association learning and risk association selection; and outputting patient risk scores, identified high risk patients, risk factors for risks and risk groups, and risk groups and risk associations; and calculate a risk score for an individual patient using the trained model comprising steps of: receiving individual features comprising patient information; performing the linkage regularization using the received individual features; and outputting a patient risk score for one or more target risk types for the individual patient for display via a device providing a user interface.

In a further aspect, there is provided a computer program product for performing operations. The computer program product includes a storage medium readable by a processing circuit and storing instructions run by the processing circuit for running a method. The method is the same as listed above.

BRIEF DESCRIPTION OF THE DRAWINGS

These and other objects, features and advantages of the present invention will become apparent from the following detailed description of illustrative embodiments thereof, which is to be read in connection with the accompanying drawings, in which:

FIG. 3 depicts a formulaic algorithm to perform the Linkage Regularization portion of the method of FIG. 1 according to an example embodiment;

FIG. 5 shows example Identified Risk Factors for use in the model in an example embodiment;

DETAILED DESCRIPTION

With the ever-growing elderly population, the care burden and expenses for elderly population are increasing rapidly. Different from the general population, elderly people may suffer from conditions across multiple vulnerability domains and need comprehensive care service. Comprehensive Geriatric Assessment (CGA) is a multidisciplinary process that identifies problem and limitation across multiple domains of a frail older person. CGA is performed in two parts, training and individual patient assessment.

Figure 1:
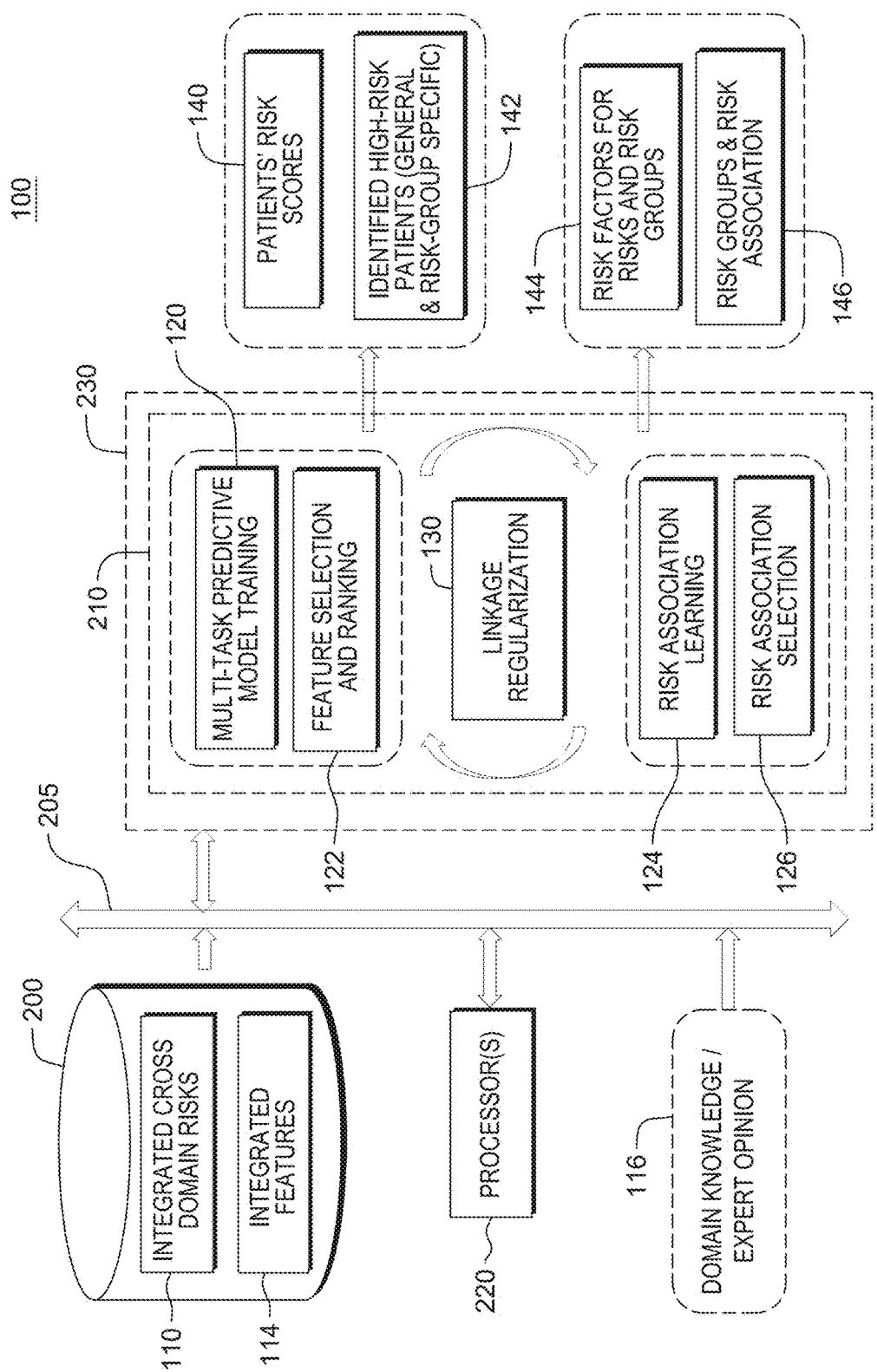
FIG. 1 shows a general system diagram of a computing system providing the training portion for the proactive Comprehensive Geriatric Assessment (CGA) system according to one embodiment.

As shown in FIG. 1, there is provided a computer-implemented system 100 for performing a training portion of a comprehensive method for proactive CGA screening. This proactive CGA screening leverages association between vulnerability domains and predicts multiple risks simultaneously. Active risk factors and vulnerability domain associations are also identified, enhancing knowledge in elderly care.

FIG. 1 shows one embodiment of a computing system 100 including one or more processing devices 220 that runs one or more software programs 210 stored in a memory storage device 230, e.g., a RAM, ROM, disk drive storage, for performing the training portion of a comprehensive model for proactive CGA screening as described herein. Further associated with system 100 is a further memory storage device, e.g., a database 200, that provides the detailed input data content/information such as medical records data pertaining geriatric data to be processed by the software program. The system 100 processors may be embodied in a computing device, e.g., desktop, laptops, services, mobile devices, that may accessible via networked and/or cloud communications infrastructure, e.g., via a LAN, WAN, wireless and/or wired public or private communications network, e.g., via the internet or virtual private network (not shown).

Further, the memory storage device 230 for the computing system 100 to generate and use a geriatric risk screening model for risk screen detection comprises, e.g., a main memory and/or a cache level memory, and the hardware processor(s) 220 or like computation device are coupled to the memory, e.g., via a data and address bus 205. The processor device 220 is configured to execute computer program code 210 to perform the methodologies for risk screen detection. In one aspect, the associated memory storage device 230 receives and stores program code 210 including the functions and procedures that are accessed by the hardware processor device 105 for configuring the hardware processor device 220 to build and utilize a risk screen prediction model including a linkage regularizer component for mapping a patient's geriatric features including integrated cohorts and risk domains to a risk prediction(s) for one or more risk domains, e.g., cognitive, behavioral, functional, etc. The hardware processor device 220 is particularly configured to apply a learned model and communicate outputs for a medical professional, e.g., a doctor or caregiver, etc. via an interface display device.

In one embodiment, the system 100 receives data from multiple patients from data storage 200, including but not limited to: patient data can include electronic medical records, e.g., diagnosis, laboratory results, medications, procedures, etc., questionnaire data, genetics information, activity tracking, nutrition (diet) tracking information, etc. This data may be further accessed and received via a local network, e.g., private or public network, via a network input/output interface for use by the hardware processor device 220 in building/applying the Linkage Regularizer.

More specifically, in the embodiment of FIG. 1, system 200 processing device 220 runs software program 210 to receive input data comprising: Integrated Cross Domain Risks 110 and Integrated Features 114. In one embodiment, Domain Knowledge data and/or Expert Opinion data on risk association 116 can also be input. Integrated Cross Domain Risks 110 can include risk targets labels, and Integrated Features 114 can include candidate risk features for model training. Both Integrated Cross Domain Risks and Integrated Features can include partially observed values and/or missing values.

The data is input to a Linkage Regularization program 210 running in a computer system 100 that comprises the following modules. One module is Multi-task predictive model training 120 that runs to simultaneously predict multiple risks across multiple vulnerable domains, and performs leveraging association between risks and vulnerability domains. Another module is Risk factor selection and ranking 122 that formulates as sparsity constrains to identify active factors for individual risks and vulnerability groups Risk association learning. Yet another module is Risk association learning 124 that learns association between risks using intermediate results from the multi-task predictive model, and capable to incorporate prior knowledge. Still another module is Risk association selection 126 that performs novel sparsity regularization to leverage information from the predictive model.

In one embodiment, upon completion of the Linkage Regularization 130, data is output via a user interface, e.g., a display device, as follows: Patient Risk (i.e., predicted risk) Scores 140, Identified High Risk Patients (general and risk-group specific) 142, Risk Factors for Risks and Risk Groups 144 and Risk Groups and Risk Association 146. For example, using the model will be able to evaluate a risk of falling, e.g., within the next two years, for an elderly patient, e.g., a functional risk. An example of a cognitive risk is whether an elderly patient is able to remember a date or month, and a behavioral risk evaluates whether a risk that an elderly patient is/becomes agitated.

Figure 2A:
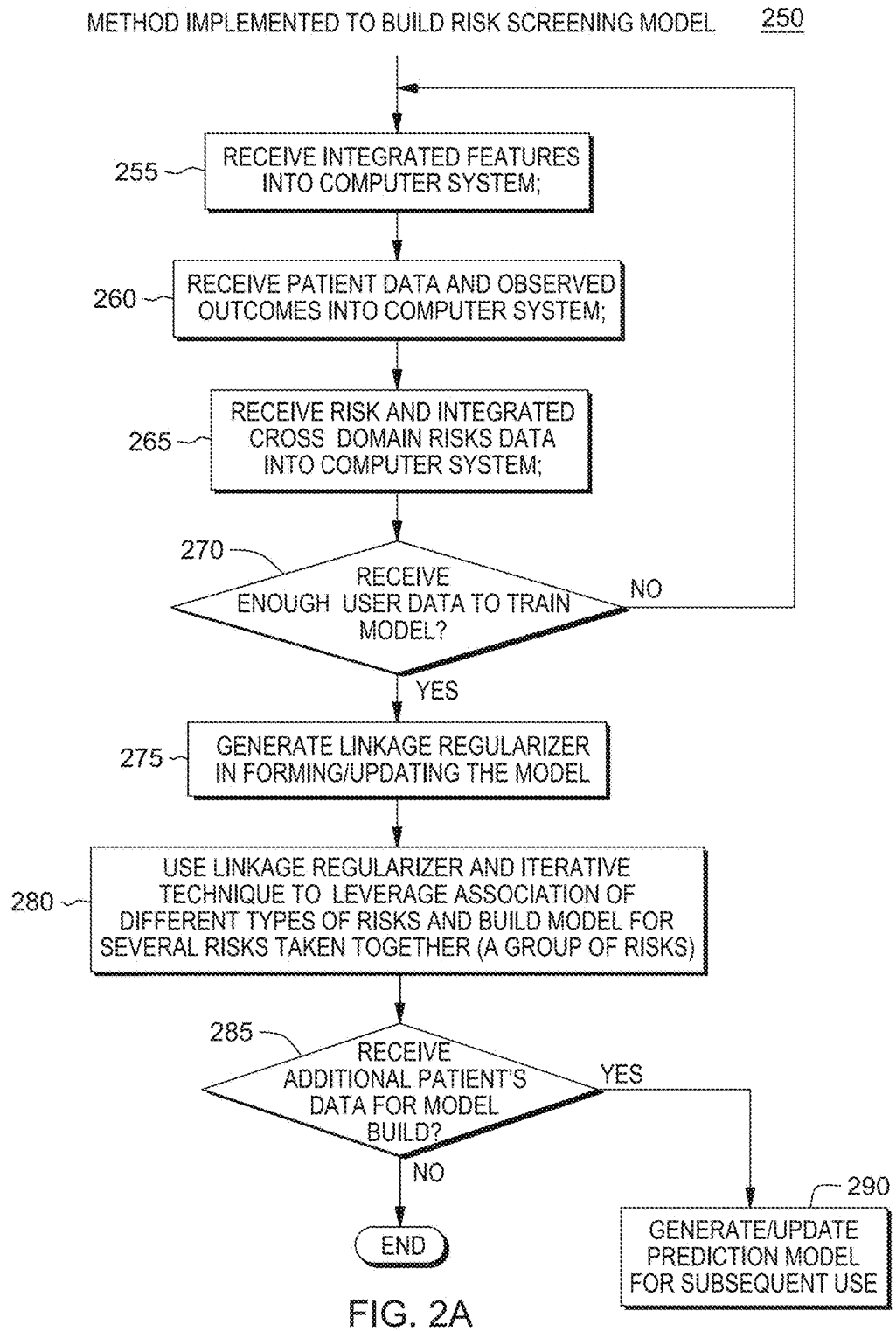
FIG. 2A shows a computer-implemented method for training the geriatric risk screening model for proactive CGA screening in one embodiment.

FIG. 2A shows a computer-implemented method 250 for training the geriatric risk screening model for proactive CGA screening. The method 255 performed by the system 100 includes receiving existing features data of multiple patient(s), e.g., age, physical/mental characteristics, injuries, illnesses (diseases) or like infirmities. Additional inputs at 255 may include receipt of survey data including patients' characteristics and answers to survey questions. Exemplary survey questions may include, but are not limited to:

whether the patient have difficulty preparing meals; Whether the patient receive home health care in the last 12 months; The number of living sisters the patient has; How often does the patient see his/her children; Whether the patient has trouble seeing things; Whether the patient had shortness of breath in the last 12 months; Whether the patient has regular exercise routine; Whether the patient had flu shot in the last 12 months; What the patient's income level is.

Additionally input to the system at 260 is patient observations data that has been collected for the multiple patient(s) over a predetermined period of time, e.g., 2 years. During this time period, observations are recorded from which it is determined whether the patient had exhibited a particular functional or cognitive behavior, e.g., became depressed, or succeeded/failed at a particular task, e.g., fell or failed to remember a date. At 265, these integrated features and observed outcomes for patients aggregated over this time period are input to the model.

Optionally received and input to the model at 265 are integrated cross domain risks data which data represents known or existing knowledge about the association of different types of risks, e.g., cognitive risk is highly associated is with a functional risk, and behavioral risks are not associated highly associated with cognitive and functional risks.

At 270, a determination is made as to whether there is enough input patient data to train the predictive risk screening model. If not enough information is present the method returns to step 255 for receiving more input and/or more observations data. Otherwise the process continues to 275 for building the model.

Generally, the model build approach is referred to as Linkage (LINKed tArgets reGrEssion), which models comprehensive risk prediction as a sparse optimization problem. Linkage builds a sparse linear predictor for every risk target, and assumes that the sparsity patterns on the coefficients of the linear predictors are similar for similar risks. Actually the sparsity pattern, i.e., the nonzero elements of the linear predictor coefficients reflect the "active" features that really contribute to the predicted risk. Therefore the method assumes similar risks should have similar contributed features. Linkage learns a task association matrix from data.

The model build implements an efficient alternating optimization procedure at 280 to solve the problem and validate its effectiveness on both synthetic and real world data sets.

At 270, FIG. 2A, the predictive geriatric risk screening model is generated. The formed model consider the problem of jointly predicting m risks for n observations (or samples, patients).

A general structure of the model is $X \times \beta = Y$ where X is the input features, characteristics and features of multiple patients, $\beta$ is a coefficient matrix representing where each column of $\beta$ represent the weights of different types of characteristics for one type of risk and target matrix Y are the observed risk targets (risk scores) for the input patients. In training the model, there is optimally determined the values of coefficient matrix $\beta$ and determine values of a matrix $\Omega$ representing the risk associations among the columns of $\beta$. Returning to FIG. 1, in Linkage Regularization program 210 there is run a global iteration process where modules 120, 122 run steps to leverage information in $\Omega$ to improve $\beta$; and modules 124, 126 are the steps to leverage information in $\beta$ to improve $\Omega$. The linkage regularizer 131 of FIG. 3 is the component that connects these steps.

For the model build phase, there is defined $y_j \in R^{n \times 1}$ as the vector of the j-th risk target, and $Y=[y_1, \ldots, y_m] \in R^{n \times m}$ be a target matrix. Assuming there are d features and given that $x_i \in R^{n \times 1}$ is the i-th feature vector, then $X=[x_1, \ldots, x_d] \in R^{n \times d}$ be the feature matrix. In one embodiment, it is assumed that both X and Y are completely observed. In EHR or healthcare related data sets, it is common that risk targets or features are incompletely observed. Different risks or features could be observed for different groups of samples, or they could partially share a group of samples.

For each risk target, there is considered the following generalized linear model:

$$E(y_j|X)=g^{-1}(Xw_j),$$

where $E(\cdot)$ denotes expectation, $g(\cdot)$ is the link function, $w_j \in R^{d \times 1}$ is the coefficient vector of target j, and $Xw_j$ is the linear predictor. The coefficient matrix is collectively denoted as $W=[w_1, \ldots, w_m] \in R^{d \times m}$. Each column of W contains the coefficients of one risk target, and each row contains the coefficients of one feature in the m targets. The link function $g(\cdot)$ describes the relationship between the mean of target response $y_j$ and features X. Depending on the type of target response $y_j$, there are many commonly used link functions. In one embodiment, two types of risks are considered: continuous risks and binary risks, each having a corresponding link function.

In one embodiment, there is determined a hidden association between risk targets by assuming that the risk association is revealed in the structure of the coefficient matrix W. In relation to multi-task learning, representations of target relatedness are categorized into two types. Methods belong to the first type use the sparsity patterns of $w_j$'s to reflect target relatedness. Related targets are assumed to share the same group or similar groups of features. Methods in a second type use the covariance matrix of W to characterize risk association. These two different representations are blended into a unified framework. Both the sparsity pattern and the covariance matrix of W are used to characterize risk associations.

In one embodiment, it is assumed that the coefficient matrix W follows a Matrix Variate Normal (MVN) distribution wherein:

$$W \sim MVN(0, \Gamma, \Omega)$$

where the first term "0" is a d-by-m matrix of zeros representing the location of W. The second term $\Gamma$ is a d-by-d matrix representing the row-wise covariances of W. In one embodiment, there is set $\Gamma = c^2 I$, where $c^2$ is unknown, and is transformed into a tuning parameter in the objective function. By setting $\Gamma$ to be a diagonal matrix, it is assumed that rows of W are independent with each other. In other words, coefficients of different features in the same target are not correlated. This assumption can be relaxed without adding too much complexity to the model. The third block of parameter $\Omega$ is a m-by-m symmetric positive definite matrix with $\Omega$ representing the column-wise covariance of W. It is unknown and reflects risk association. In the field of health-care informatics, domain knowledge about risk association is often available or partially available. In order to utilize available domain knowledge, there is imposed a prior distribution on $\Omega$:

$$\Omega \sim IW(\alpha\Omega_0, v),$$

where IW denotes the Inverse-Wishart distribution, $\alpha$ and $v$ are two tuning parameters, and $\Omega_0 \in R^{m \times m}$ is a known symmetric positive definite matrix. $\Omega_0$ includes assigned values representing all prior knowledge about risk association (existing domain knowledge and/or expert opinion input), e.g., whether risks are strongly associated with each other or weakly associated. When domain knowledge on risk association is available, the prior distribution can leverage the information and help improve the estimation of. When domain knowledge about risk association is not available, $\Omega_0$ is set to be $\delta I$, where $\delta$ is an arbitrary small value. In both cases, $\Omega_0$ is positive definite. Combining each of the models, the full likelihood of W and $\Omega$ is expressed as follows:

$$p(W,\Omega|X,Y,\Omega_0) \propto p(W|X,Y,\Omega)p(\Omega|\Omega_0).$$

A Maximum Like Estimation (MLE) is used to estimate the coefficient matrix W and risk association matrix $\Omega$. As the sparsity pattern of W also reflects risk association, to enforce sparsity of W, there is added an additional $l_1$ regularizer on W.

Referring to FIG. 2A, at 275, as the structures of W and $\Omega$ are closely related, e.g., highly correlated risks may have similar groups of "active" features, and coefficients of two related risks may be similar, there is imposed a Linkage regularizer, to link the two components. The Linkage regularizer is given as follows:

$$pen(\gamma, \Omega, W) = \gamma \sum_{i \neq j} |\Omega_{ij}| \|w_i - \text{sign}(\Omega_{ij}) w_j\|_1$$

where the notions $|\cdot|, \|\cdot\|_1$ and $\text{sign}(\cdot)$ denote the absolute value, the $l_1$ norm, and the sign function, respectively. Both W and are unknown and needed to be estimated.

Then, at 280, for the model build, the Linkage regularizer links the two components W and $\Omega$ and let them reciprocally leverage information from each other.

FIG. 3 shows a formulaic algorithm depicting the operations of the Linkage Regularizer model 130 run on computer system 100. The Linkage Regularizer component 131 minimizes or optimizes a loss function. Toward that end, the Linkage Regularizer links the two components, the coefficient matrix W (indicated as $\beta$ in FIG. 3) and the risk association matrix $\Omega$.

The following formulaic algorithm (shown in FIG. 3) is an optimization problem solved with the Linkage Regularizer:

$$\min_{\beta,\Omega} l(Y, X, \beta) + tr\left[\left(\frac{\lambda_1}{2}\beta^T\beta + \frac{\lambda_2}{2}\Omega_0\right)\Omega^{-1}\right] + \frac{\lambda_3}{2}\text{logdet}(\Omega) +$$
$$\gamma_1 \sum_{i \neq j} |\Omega_{ij}| \|\beta_i - \text{sign}(|\Omega_{ij}|)\beta_j\|_1 + \gamma_2 \|\beta\|_1, \text{ s.t. } \Omega \geq 0.$$

where the first term $l(\cdot)$ denotes the loss function, which is derived from the negative log-likelihood function of the generalized linear model $E(y_j|X)$; the tr and det denote the trace and determinant of a matrix, respectively; $\lambda_1$, $\lambda_2$, $\lambda_3$, $\gamma_1$, and $\gamma_2$ are tuning parameters.

In one embodiment, The loss function term $l(\cdot)$ depends on the choice of link function in the generalized linear model, which further depends on the types of risks: continuous risk and binary risk. When the support of $y_{ij}$ spans the whole real line, i.e. $y_{ij} \in -\infty, \infty$, risk j belongs to the continuous type. In this case $y_{ij}$ is assumed to follow a Gaussian distribution, and the corresponding link function is the identity function. The loss function can be written as follows:

$$l_{ij} = l(y_{ij}, x_{(i)}, w_j) = \frac{1}{2} \|y_{ij} - x_{(i)} w_j\|_2^2,$$

where $x_{(i)}$ denotes the i-th row of X, and $\|\cdot\|_2$ denote the $l_2$ norm. When $y_{ij}$ only have two possible outcomes, i.e. $y_{ij} \in \{1,1\}$, risk j belongs to the binary type. In this case, $y_{ij}$ is assumed to follow a Bernoulli distribution. The corresponding loss function can be written as follows:

$$l_{ij} = l(y_{ij}, x_{(i)}, w_j) = \log(1 + \exp(-y_{ij} x_{(i)} w_j)).$$

Letting L be a n-by-m matrix where the (i, j)-th element $l_{ij}$ is defined in either form as above. Letting $\vec{1}_m$ denote a m-dimensional vector of all 1s. The loss function then is defined as the summation of $l_{ij}$ across all i (observations) and all j (risks). The loss function can be expressed as follows:

$$l(Y, X, W) = \vec{1}_n^T L \vec{1}_m = \sum_{i=1}^{n} \sum_{j=1}^{m} l(y_{ij}, x_{(i)}, w_j).$$

When all risk targets belong to the continuous type, the model is a continuous model; when all risk targets belong to the binary type, the model is a binary model; when both types of risk targets exist, the model is referred to as a mixed model.

It is understood that assume that both X (features) and Y (risk targets) may be completely observed. However, as incomplete observations are ubiquitous in healthcare data, e.g., particularly when jointly predicting multiple risks (where it is often expensive, or impossible to obtain all information from all samples/patients) incomplete observations may be dealt with in risk targets (Y) and features (X) using different methods, e.g., unobserved values in X may be imputed in advance using off-the-shelf imputation methods, such as the K-nearest-neighbor method.

Solving the optimization problem 130 shown in FIG. 3 is non-trivial. The Linkage Regularizer component 130 of FIG. 1 runs a global iteration component in which W and $\Omega$ are updated alternatively using an Algorithm 1 and Algorithm 2. In finding a solution an iterative algorithm, Algorithm 1, updates W, wherein at each iteration, the two blocks W and $\Omega$ are updated alternatively. In one embodiment, a Smoothing Proximal Gradient (SPG) method is used to update W. Algorithm 1 that is run for solving the optimization problem at step 180, FIG. 2A, includes:

Require: $\Omega = \Omega^{(t-1)}$ from a last global iteration, and data set X, Y, regularization parameters $\lambda_1$, $\gamma_1$, $\gamma_2$, and $\mu$, where $\mu$ is a parameter in the SPG method and controls how close the proximal gradient is to the original objective function:

1: Initialize $\beta^{(0)} = W^{(t-1)}$

2: for k=0, 1, 2, ... until convergence of $\beta^{(k)}$ do

3: Formulate a matrix $C_{(i,j),k}$ according to equation (1) below

4: Compute $\nabla h(W^{(t-1)}) = \nabla l(W^{(t-1)}) + \lambda_1 W^{(t-1)^T} \Omega^{-1} + (A^*)^T C$ 5: Line search for step size $\eta$ 6: Compute $$V = \beta^{(k-1)} - \frac{1}{\eta} \nabla h(W^{(t-1)})$$

7: Update $\beta^{(k)}$ according to equation (3) below

8: end for

9: Update $W^{(t)} = \beta^{(k)}$ where k is initially set at zero (0) and is the index of inner iteration. Every time the program runs through steps 3-7 of Algorithm 1, k is incremented by 1; and where η is the step size in the inner iteration and is calculated by the Armijo-Goldstein method (i.e., backtracking line search). Here, in the $t^{th}$ global iteration, we fix $\Omega=\Omega^{(t-1)}$ and update W. When $\Omega$ is fixed, the Linkage regularizer reduces to the Graph-guided Fussed Lasso regularizer. Then, a Smoothing Proximal Gradient (SPG) method may be used to solve the optimization problem.

Reformulating the Linkage regularizer as $\max\|A\|_{\infty \leq 1} \langle CW^T, A \rangle$, where A is an auxiliary matrix, $\|\cdot\|_\infty$ is the $l_\infty$ norm, and C is a m(m-1)-by-m matrix and is defined according to equation (1) as follows:

$$C_{(i,j),k} = \begin{cases} \gamma_1 |\Omega_{ij}| & \text{if } k = i, \\ \gamma_1 \text{sign}(\Omega_{ij})|\Omega_{ij}| & \text{if } k = j, \text{ and} \\ = 0, & \text{otherwise.} \end{cases} \quad (1)$$

A smooth approximation to the Linkage regularizer may then be constructed. Replacing the linkage regularizer with the smooth approximation a further optimization problem is formed and using the proximal method, is solved by iteratively solving the following problem set forth in equation (2) as follows:

$$\min_W \frac{1}{2}\|W - V\|_F^2 + \frac{\gamma_2}{\eta}\|W\|_1 \quad (2)$$

where $\|\cdot\|_F$ denotes the Frobenius norm, η is the step size, and $$V = W^{(k-1)} - \frac{1}{\eta}\left[\nabla wl(Y, X, W^{(k-1)} + \lambda_1 W^{(k-1)^T} \Omega^{-1} + (A^*)^T C\right]$$

To distinguish from the global iteration, this iteration is referred to as the inner SPG iteration. $W^{(k-1)}$ is the solution obtained from the previous inner SPG iteration, and q is the step size. The Iterative Shrinkage-Thresholding Algorithm (ISTA) with a backtracking algorithm may be used to decide η which is the step size in the inner iteration that controls how far away the updated $W^{(k)}$ is from the W in the last iteration, i.e., $W^{(k-1)}$.

Problem of equation (2) can be solved by applying a soft-thresholding rule to each element of V. The solution is given according to equation (3) as follows:

$$W_{i,j}^{(t)} = \begin{cases} V_{i,j} - \frac{\gamma_2}{\eta} & \text{for } v_{i,j} \geq \frac{\gamma_2}{\eta} \\ V_{i,j} + \frac{\gamma_2}{\eta} & \text{for } v_{i,j} \leq -\frac{\gamma_2}{\eta} \\ = 0, & \text{otherwise} \end{cases} \quad (3)$$

where $v_{i,j}$ is the regularization parameter for the (i,j)-th moment of W. The larger $v_{i,j}$, the larger shrinkage will be applied to the (i, j)-th moment of W. In the global iteration performed at step 280, FIG. 2A, solving the optimization problem includes running the second algorithm (Algorithm 2) for updating $\Omega$ in accordance with an asymmetric thresholding rule. Once W is updated in Algorithm 1, it is temporarily fixed. Algorithm 2 is the method to update $\Omega$.

Note that when $\Omega$ is updated using Algorithm 2, W is fixed. Algorithm 2 steps for solving include:

Require: $W^{(t-1)}$ from last iteration, regularization parameters $\lambda_1, \lambda_2, \lambda_3, \gamma_1$, and $$Q = \frac{\lambda_1}{2}(W^{(t)})^T W^{(t)} + \frac{\lambda_2}{2}\Omega_0$$

1: Initialize $\Lambda^{(0)} = \Omega^{(t-1)}$
2: for k=0, 1, 2, . . . until convergence do
3: Set $\Sigma^{(0)} = \Lambda^{(k-1)}$
4: for i=0, 1, 2, . . . until convergence do
5: Compute U according to (4) and line search for η
6: Apply the asymmetric soft thresholding rule to off-diagonal elements of U and update $\Sigma^{(i)}$
7: end for
8: Update $\Lambda^{(k)} = \Sigma^{(i)}$
9: end for
10: Update $\Omega^{(t)} = \Lambda^{(k)}$ where U is computed according to equation (4) which is an optimization problem iteratively solved within the $k^{th}$ outer iteration using the proximal method and is referred to as an inner iteration. The optimization problem is set forth according to equation (4) as follows:

$$\min_\Sigma \frac{1}{2}\left\|\sum - U\right\|_F^2 + pen\left(\frac{\gamma_1}{\eta}, \Sigma, W\right) \quad (4)$$

where $$U = \Sigma^{(i-1)} - \frac{1}{\eta}\left[\frac{\lambda_3}{2}(\Sigma^{(0)})^{-1} - (\Sigma^{(i-1)})^{-1} Q(\Sigma^{(i-1)})^{-1}\right]$$

$\|\cdot\|_F$ denotes the Frobenius norm, η is the step size, and $\Sigma^{(i-1)}$ denotes the solution from the last inner iteration, and where this optimization problem make use of the linkage regularizer 131 given according to the following:

$$pen(\gamma, \Omega, W) = \gamma \sum_{i \neq j} |\Omega_{ij}| \|w_i - \text{sign}(\Omega_{ij}) w_i\|_1$$

The notions $|\cdot|, \|\cdot\|_1$ and sign(·) denote the absolute value, the $l_1$ norm, and the sign function, respectively.

Thus, in the method run at 280, FIG. 2A, both W and $\Omega$ are estimated. It is understood that in the global iteration, Algorithms 1 and 2 are applied alternatively until a convergence criteria is met, i.e., when the relative change in the objective function between two consecutive global iterations is used as the stopping criterion.

Returning to step 285, FIG. 2A there is depicted additional optional steps of receiving, at system 100, additional patients' data that can be used for further updating the model at 290 by repeating the steps in FIG. 2A.

Figure 2B:
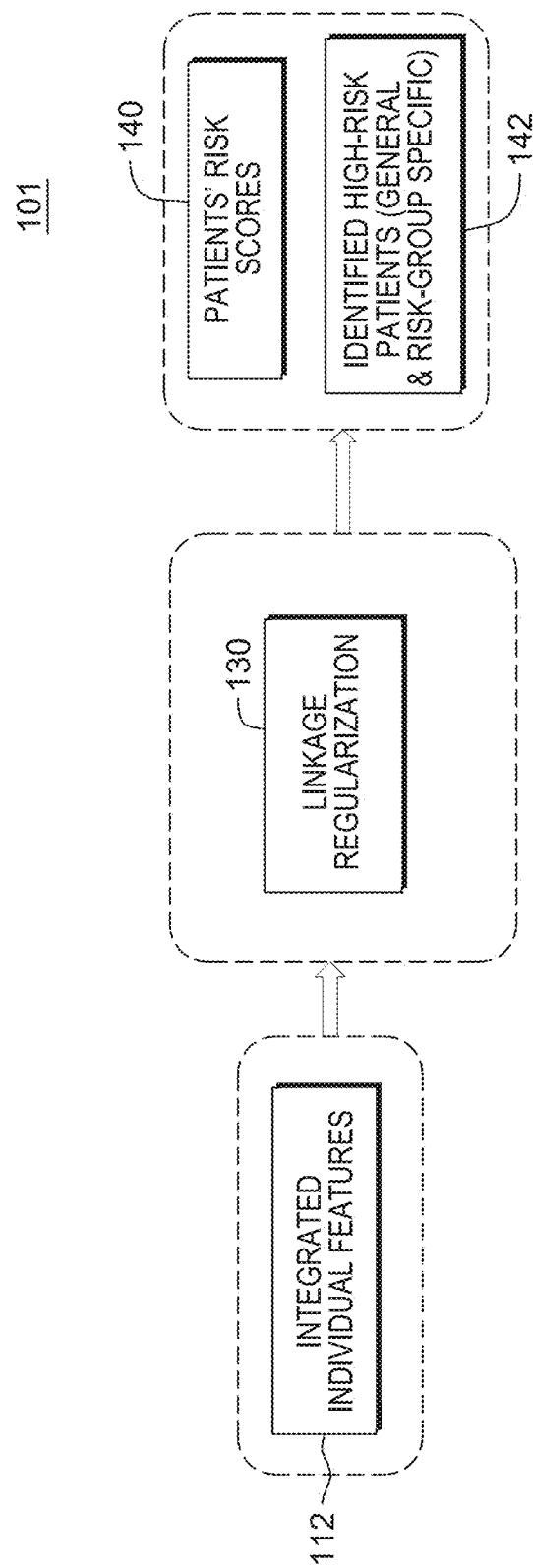
FIG. 2B shows a general method of the individual patient assessment portion of the proactive CGA according to one embodiment.

FIG. 2B shows a computer-implemented system 101 configured for performing an individual patient portion of a comprehensive method for proactive CGA risk screening. FIG. 2B shows the predictive model 130 and linkage regularizer component 131 used to predict the risk of a new individual patient as having or developing a particular problem based on inputs for that new patient. That is, there is generated a risk estimate for new patient based on new input data including integrated or individual patient Features data 112 for a single individual patient. Such Features 112 can include partially observed values and/or missing values. In one embodiment, input features/characteristics data 112 for the new patient may include that patient's characteristics (cohorts) data X (e.g., obtained data from electronic medical records, e.g., age, gender, income level, health insurance type, medical diagnosis, laboratory results, medications, procedures, etc., and survey/questionnaire answer data, genetics information, activity tracking, nutrition (diet) tracking, etc.). An input may further include a type of target risk selected by a user of the model for which a risk estimate is to be predicted. The processing by the Linkage Regularization 130 of FIG. 3 uses the model to generate the patient's risk outputs Y indicating the predicted risk value for the specified risk type and embodied as an output Patient Risk Score(s) 140 for the specific risk type selected. From the output score, the system further identifies a High Risk Patient(s) (general and risk-group specific) 142. These scores represent probabilities that the patient may have a particular functional/cognitive/behavioral risk or issue, e.g., a fall or failure to remember a date, within the specified predetermined period. This time period is commensurate with the time from which patient's observed data was collected for model training.

In one embodiment, the output generates a risk score (value) corresponding to each risk type built into the model. For example, if there are up to forty-one (41) risk factors, for a new patient's characteristics input, the model generates forty-one scores, with a single each score corresponding to a respective risk factor.

These output predicted risk and scores may be subsequently communicated to a health care professional, e.g., a doctor or caregiver, and may be used by the health care professional to provide a course of treatment or consultation, e.g., preventative treatment or otherwise, for the individual patient based on the predicted risk and scores. Additionally or alternatively, generated risk prediction(s) may be used by a health insurance company to determine coverage and premium payment levels for the particular individual based on assessed risk.

In one embodiment, the predictive risk model 130 and linkage regularizer 131 are run in system 101 to identify risk factors (feature selection), leverage information in feature coefficients ($\beta$) to improve $\Omega$, leverage information in $\Omega$ to improve $\beta$, and improve prediction performance. The two goals of predicting multiple risks and learning the relationship between risk targets are performed simultaneously.

Figure 4:
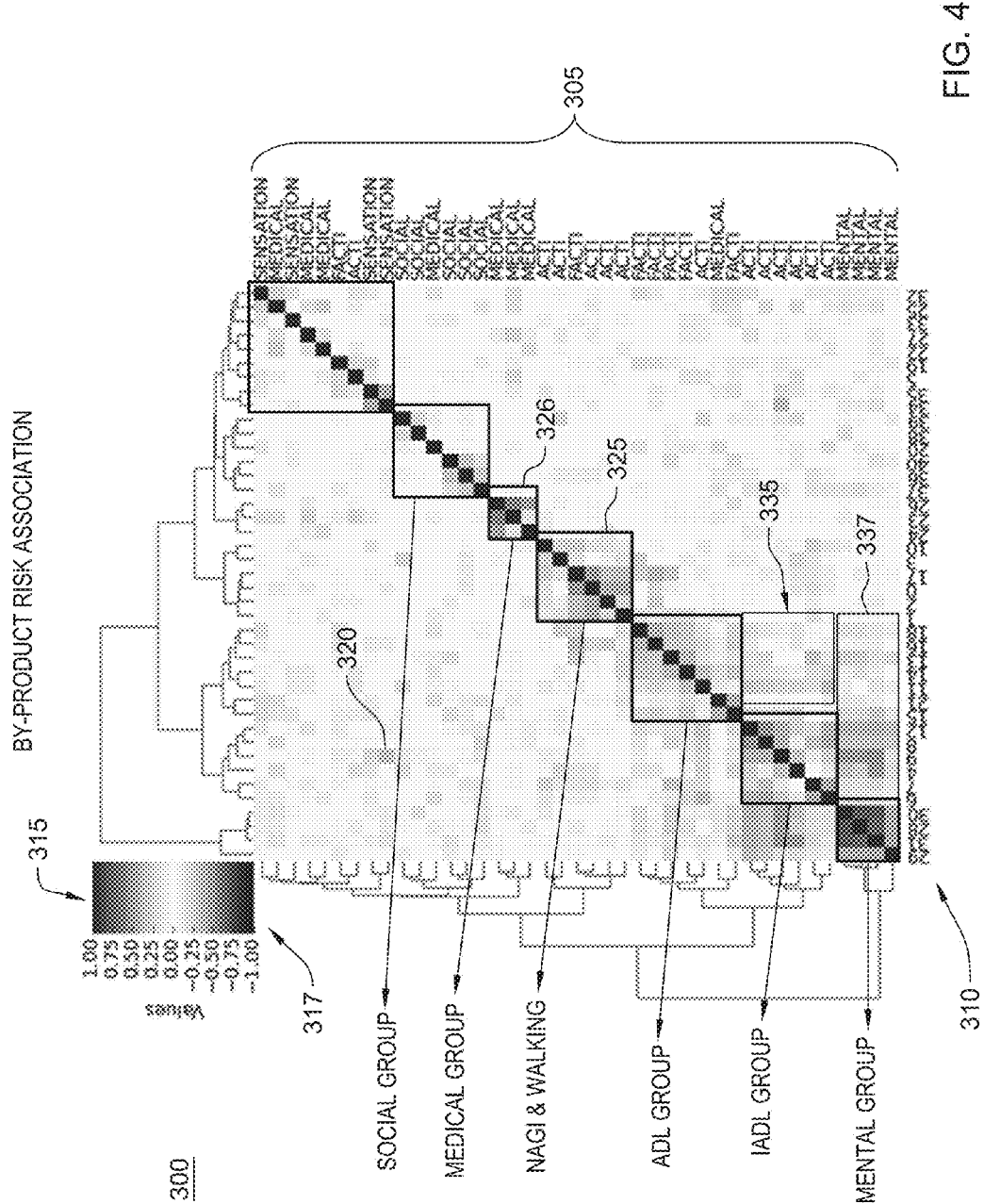
FIG. 4 shows results of computing risk associations as a by-product of implementing linkage regularization in an example embodiment.

FIG. 4 shows a graphical depiction of Risk Association outcomes 300 embodied as block diagonal matrix $\Omega$ produced after model training is performed with each block including a number of risks. These Risk Associations are shown in FIG. 4 according to various example groups or risk factors such as Social Group, Medical Group, NAGI index (which evaluates walking abilities of patients), ADL Group, IADL Group and Mental Group. These groups 325, 326, etc. are graphed along the vertical axis representing the risk domains 305, e.g., medical, social, mental, functional, sensation, vs. the specific types of risk 310 (e.g., risk factors shown as risk index values 0, . . . , 40) along the horizontal axis—each risk type belonging to a specific domain (e.g., 7 domain types). An intersection 320 between a risk type and risk domain represents a risk association having a value indicated according to a color code as depicted, e.g., the values of strong risk associations are darker values 315 and strong negative associations are shown as opposite dark values 317. Intersections indicated as lighter color shades show relative weaker positive or weaker negative associations. Along the diagonal are shown the intersections where a risk of the first column is associated with the risk domain of the first row, the risk of the second column is associated with the risk domain of the second row. The between-group correlation is indicated by values along an intersection between a selected risk domain(s) 305 and a particular risk factor(s) 310. For example, a group 335 of risk factors across several risk domains show relatively strong positive association and a group 337 of risk factors across several other risk domains show relatively strong negative association.

In particular, FIG. 5 shows Identified Risk Factors that can be used in Risk Association can include the following groups: Group 1 (Mental), Group 2 (IADL) (Instrumental Activities of Daily Living index), Group 3 (ADL) (Activities of Daily Living index), Group 4 (NAGI), Group 5 (Medical), Group 6 (Social) and Group 7 (Sensation).

Figure 6A:
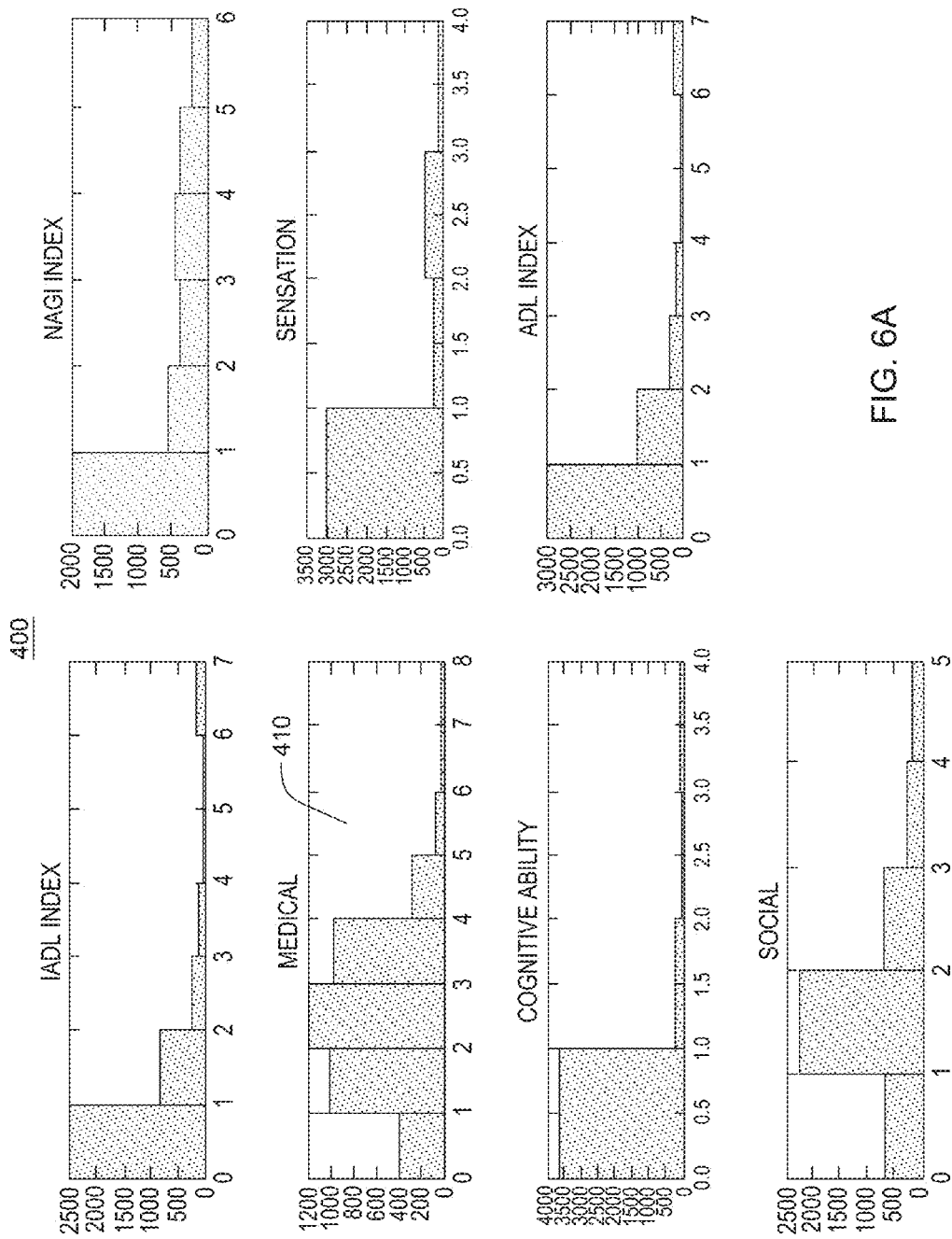
FIGS. 6A and 6B show plots representing Patients Risk Scores and risk groups in an example embodiment.

FIG. 6A shows example Patient Risk Scores outputs 400 of the Linkage Regularizer 130 according to one embodiment. Patient Risk Scores according to various indices are shown, such as IADL, NAGI, Medical, Sensation, Cognitive Ability, ADL and Social; these are based on the respective Identified Risk Factor Groups 325, 326, etc. as shown FIG. 5. FIG. 6A shows a summary of predictions after both training and individual patient analysis.

From the calculate risk scores for a new patient in each risk group there may be further identified future high-risk patients by comparison with these distributions. In FIG. 6A, for particular risks belonging to a particular domain, the corresponding scores are summed together to obtain an overall score for that domain. In an example embodiment of FIG. 6A, each plot 410 shows, for the model, a distribution of the sums of generated particular risks associated with each patient group or domain.

Figure 6B:
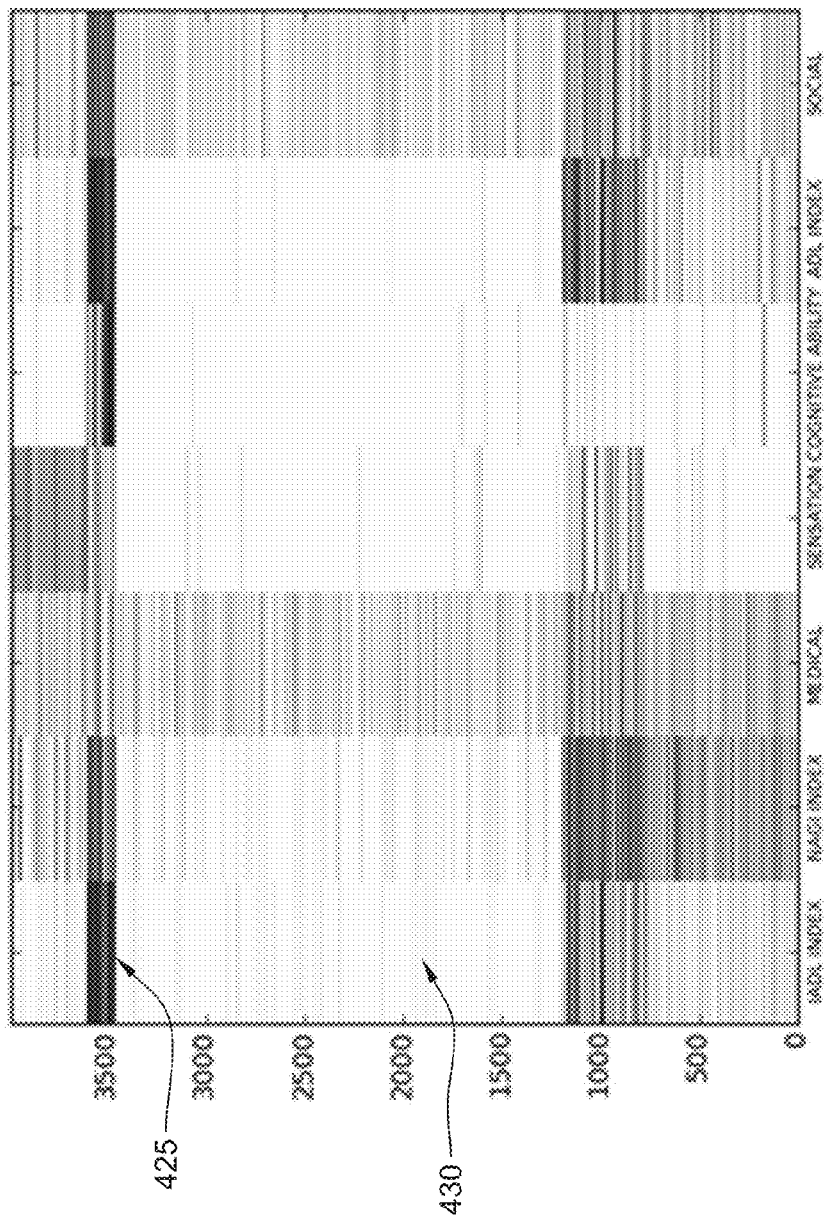

In one embodiment, each patient receives a Risk Score for all risk factors in each Domain. Patient Groups and Risk Patterns can be identified as shown in the chart on the bottom right of FIG. 6B; color indicates risk with darker colors showing increased risk. For example plot 420 depicts the manner in which identified patient groups and risk patterns are determined. For all multiple patients (rows along vertical axis) used in the training the model, there is shown the overall score values in each of the seven domains (columns along horizontal axis). Those patients having darker color shade scores 425, e.g., example high sensation risk scores, represent a High-risk group for that domain, while patients having lighter shade scores 430 represent a Low-risk group for that domain.

Figure 7:
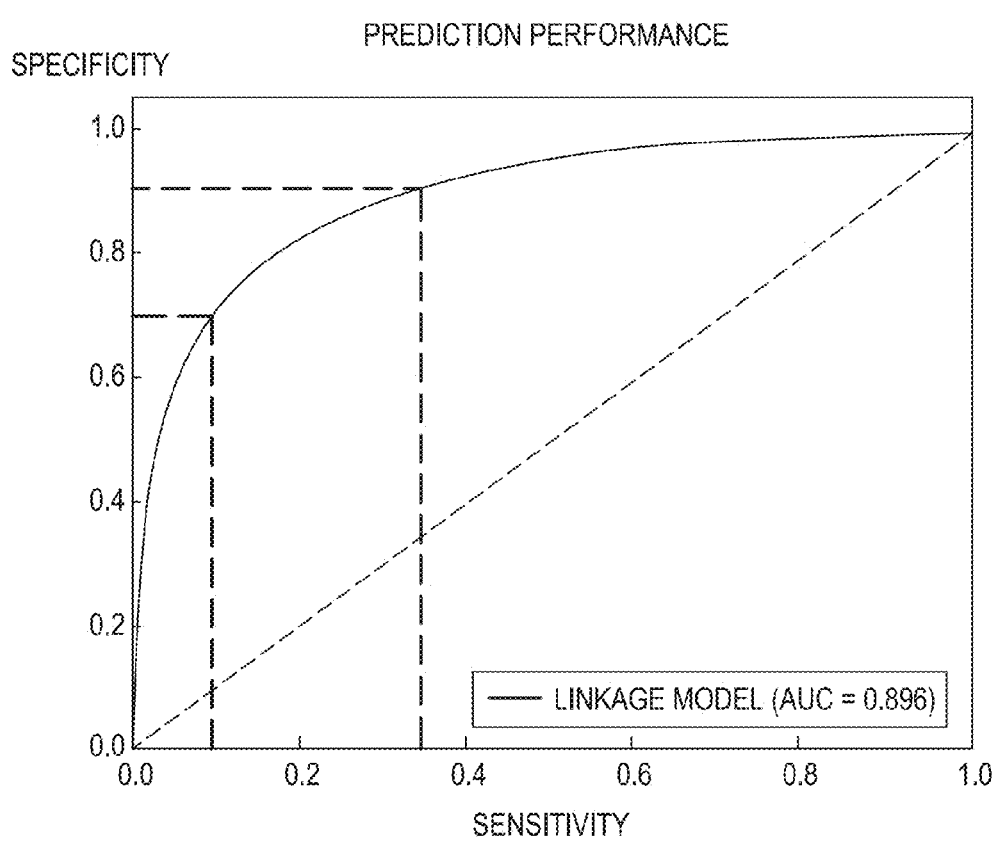
FIG. 7 shows a comparison of example prediction performance results using linkage regularization model versus traditional screening techniques.

FIG. 7 shows Prediction Performance of the Linkage Regularizer in one embodiment, illustrating how well the Linkage Regularizer 130 works in comparison with traditional screening tools. Screening tools typically trade-off between sensitivity and specificity. As shown in FIG. 7, traditional screening tools may report best prediction performance of sensitivity at 71%, and of specificity at 66%. In contrast, the prediction model results exhibit a trade-off between sensitivity and specificity, i.e., when maximizing the specificity (Y-Axis) is desired, Linkage Regularizer can have Sensitivity of 70% (X-Axis) with Specificity of 90%. When maximizing sensitivity is desired, Linkage Regularizer can have Sensitivity of 90% with Specificity of 65%.

Figure 8:
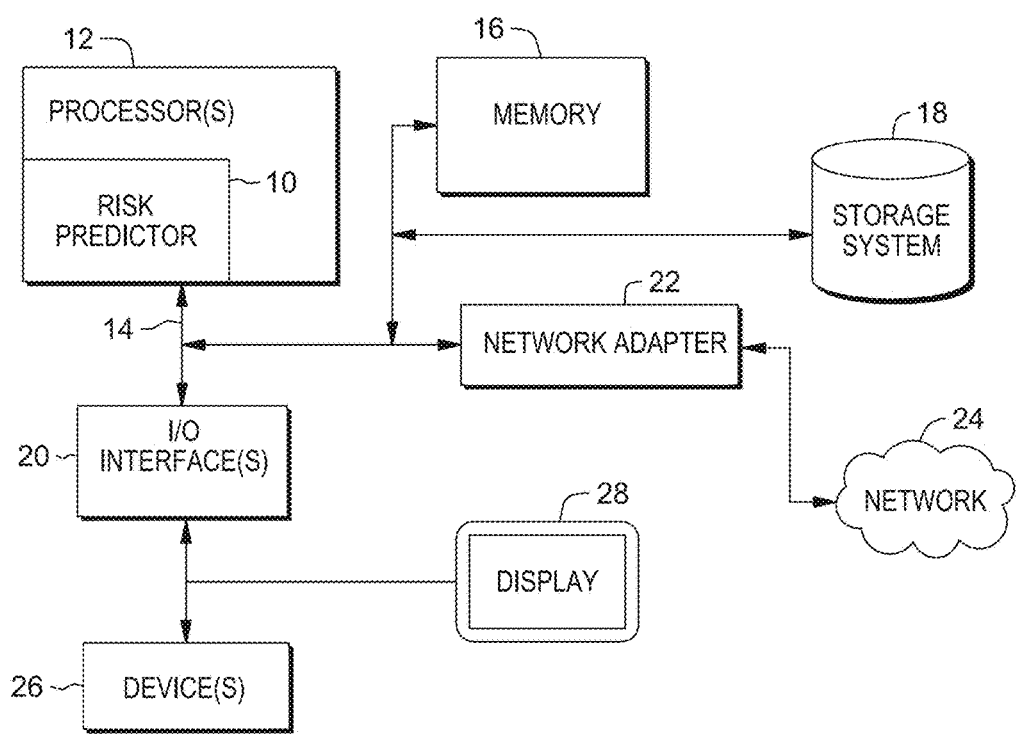
FIG. 8 depicts an exemplary hardware configuration for performing methods such as described herein.

FIG. 8 illustrates a schematic of an example computer or processing system that may implement CGA screening in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 8 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a module 10 that performs the risk screening methods described herein. The module 10 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method of performing proactive comprehensive geriatric risk screening comprising:
   receiving at a processing device, individual features data of a patient being assessed for multiple risk types;
   running, by the processing device, a multi-task predictive model trained to jointly predict multiple target risk types for said individual based on said individual features data and predict a set of risk associations by determining correlations between target risk types,
   said multi-task predictive model trained based on:
      data representing risks across multiple vulnerability domains,
      data representing features of multiple patients, and
      data representing complete or incomplete observations in risk targets and features of said multiple patients; and trained based on
   optimizing, at the processing device, a linkage regularization using the features data, the risks across multiple vulnerability domains data and said complete or incomplete observations data, said linkage regularization regulating said multi-task predictive model training, a selecting and ranking of said risk features, and a learning and selecting the set of risk associations, by linking a coefficient matrix relating target features and risk types used in said predictive model and a covariance matrix representing domain knowledge on risk associations; and calculating, by the processing device, a risk score for said jointly predicted multiple target risk types for said individual patient using said trained model and said linkage regularization optimizing; and outputting said patient risk score for each said multiple target risk types in each domain for said individual patient for display via a device providing a user interface; and providing, based on the predicted patient risk score for said multiple target risk types, a course of preventative treatment for the individual patient.

2. The method of claim 1, wherein said optimizing said linkage regularization comprises:

performing an iterative algorithm on said risk feature selection and ranking;

applying a thresholding rule to update elements of the covariance matrix representing domain knowledge on risk associations used by the iterative algorithm for the risk feature selection and ranking; and leveraging said performing the iterative algorithm and said applying the thresholding rule.

3. The method of claim 2, wherein said iterative algorithm comprises: running a smoothing proximal gradient algorithm.

4. The method of claim 1, wherein the training further comprises: receiving one or more of expert opinion data, and domain knowledge on risk association data.

5. The method of claim 1, further comprising: determining, by said processor, whether a score of a particular risk target for said individual patient is one of: a high-risk score or low risk score.

6. The method of claim 1, wherein the individual features comprise at least one of electronic medical records, answer data from a questionnaire administered to said patient, genetics information, activity data, and diet tracking.

7. An apparatus for performing proactive comprehensive geriatric risk screening, the apparatus comprising:

a memory storage device storing a program of instructions;

a processor device receiving said program of instructions to configure said processor device to:

receive individual features data of a patient being assessed for multiple risk types;

run a multi-task predictive model trained to jointly predict multiple target risk types for said individual based on said individual features data and to predict a set of risk associations by determining correlations between target risk types, said multi-task predictive model trained based on:
data representing risks across multiple vulnerability domains,
data representing features of multiple patients, and
data representing complete or incomplete observations in risk targets and features of said multiple patients; and trained based on
optimizing linkage regularization using the features data, the received risks across multiple vulnerability domains data and said complete or incomplete observations data, said linkage regularization regulating said multi-task predictive model training, a selecting and ranking of the risk features, and a learning and selecting of the set of risk associations, said linkage regularization linking a coefficient matrix relating target features and risk types used in said predictive model and a covariance matrix representing domain knowledge on risk associations; and calculate a risk score for said jointly predicted multiple target risk types for said individual patient using said trained model and said linkage regularization optimizing; and output said patient risk score for each said multiple target risk types in each domain for said individual patient for display via a device providing a user interface; and provide, based on the predicted patient risk score for said multiple target risk types, a course of preventative treatment for the individual patient.

8. The apparatus of claim 7, wherein the processor device is further configured to:

perform an iterative algorithm on said risk feature selection and ranking;

apply a thresholding rule to update elements of the covariance matrix representing domain knowledge on risk associations used by the iterative algorithm for the risk feature selection and ranking; and leveraging said perform the iterative algorithm and said apply the thresholding rule.

9. The apparatus of claim 8, wherein said iterative algorithm comprises a smoothing proximal gradient algorithm.

10. The apparatus of claim 7, wherein the processor device is further configured to:

receive one or more of expert opinion data, and domain knowledge on risk association data.

11. The apparatus of claim 7, wherein the processor device is further configured to determine, whether a score of a particular risk target for said individual patient is one of: a high-risk score or low risk score.

12. The apparatus of claim 7, wherein the individual features comprise at least one of electronic medical records, answer data from a questionnaire administered to said patient, genetics, activity data, and diet tracking.

13. A non-transitory computer readable storage medium, tangible embodying a program of instructions executable by the computer for performing proactive comprehensive geriatric risk screening comprising:

receiving individual features data of a patient being assessed for multiple risk types;

running a multi-task predictive model trained to jointly predict multiple target risk types for said individual based on said individual features data and predict a set of risk associations by determining correlations between target risk types, said multi-task predictive model trained based on:
data representing risks across multiple vulnerability domains,
data representing features, and
data representing complete or incomplete observations in risk targets and features of said multiple patients; and trained based on
optimizing linkage regularization using the features data, the risks across multiple vulnerability domains data and said complete or incomplete observations data, said linkage regularization regulating said multi-task predictive model training, a selecting and ranking of the risk features, and a learning and selecting of the set of risk associations, said linkage regularization linking a coefficient matrix relating target features and risk types used in said predictive model and a covariance matrix representing domain knowledge on risk associations; and calculating a risk score for said jointly predicted multiple target risk types for said individual patient using said trained model and said linkage regularization optimizing; and
   outputting a patient risk score for each said multiple target risk types in each domain for said individual patient for display via a device providing a user interface; and
providing, based on the predicted patient risk score for said multiple target risk types, a course of preventative treatment for the individual patient.

14. The non-transitory computer readable storage medium of claim 13, wherein optimizing said linkage regularization comprises:
   performing an iterative algorithm on said feature selection and ranking;
   applying a thresholding rule to update elements of the covariance matrix representing domain knowledge on risk associations used by the iterative algorithm for the risk feature selection and ranking; and
   leveraging said performing the iterative algorithm and said applying the thresholding rule.

15. The non-transitory computer readable storage medium of claim 14, wherein said iterative algorithm comprises a smoothing proximal gradient algorithm.

16. The non-transitory computer readable storage medium of claim 13, wherein the training further comprises receiving one or more of expert opinion data, and domain knowledge on risk association data.

17. The non-transitory computer readable storage medium of claim 13, further comprising:
determining whether a score of a particular risk target for said individual patient is one of: a high-risk score or low risk score.

* * * * *